US009273275B2

(12) United States Patent
Kobayashi et al.

(10) Patent No.: US 9,273,275 B2
(45) Date of Patent: Mar. 1, 2016

(54) DISPOSABLE SET FOR CELL CULTURE, CELL CULTURE DEVICE AND CELL PREPARATION METHOD

(75) Inventors: Akira Kobayashi, Takasago (JP); Masaki Ichimura, Takasago (JP); Masaru Nakatani, Takasago (JP)

(73) Assignee: KANEKA CORPORATION, Osaka (JP)

( * ) Notice: Subject to any disclaimer, the term of this patent is extended or adjusted under 35 U.S.C. 154(b) by 235 days.

(21) Appl. No.: 13/807,546

(22) PCT Filed: Jun. 30, 2011

(86) PCT No.: PCT/JP2011/065064
§ 371 (c)(1),
(2), (4) Date: Dec. 28, 2012

(87) PCT Pub. No.: WO2012/002497
PCT Pub. Date: Jan. 5, 2012

(65) Prior Publication Data
US 2013/0109086 A1 May 2, 2013

(30) Foreign Application Priority Data
Jul. 1, 2010 (JP) ................................. 2010-151161

(51) Int. Cl.
*C12M 3/00* (2006.01)
*C12M 1/00* (2006.01)
*C12M 3/06* (2006.01)

(52) U.S. Cl.
CPC .................. *C12M 3/06* (2013.01); *C12M 23/44* (2013.01); *C12M 29/16* (2013.01); *C12M 47/04* (2013.01)

(58) Field of Classification Search
CPC ............................. C12M 45/04; C12M 47/02
See application file for complete search history.

(56) References Cited

U.S. PATENT DOCUMENTS 6,544,424 B1 * 4/2003 Shevitz .......................... 210/650
7,875,448 B2 * 1/2011 Furey .......................... 435/289.1
(Continued)

FOREIGN PATENT DOCUMENTS

| JP | 2001-275659 A | 10/2001 |
|----|---------------|---------|
| JP | 2004-89095 A  | 3/2004  |
| JP | 2004-344128 A | 12/2004 |
| JP | 2007-185165 A | 7/2007  |
| JP | 2008-86235 A  | 4/2008  |

OTHER PUBLICATIONS

Angele et al., "Engineering of Osteochondral Tissue with Bone Marrow Mesenchymal Progenitor Cells in a Derivatized Hyaluronan-Gelatine Composite Sponge," Tissue Engineering, vol. 5, No. 6, 1999, pp. 545-553.

(Continued)

*Primary Examiner* — Nathan Bowers
(74) *Attorney, Agent, or Firm* — Birch, Stewart, Kolasch & Birch, LLP

(57) ABSTRACT

It is an object to achieve a closed system that has a simple structure without resorting to large scale equipment and that sequentially carries out all of the step of separating useful cells, the step of culturing the useful cells separated in the separation step, and the step of washing and concentrating the cells cultured in the culturing step and to enable the preparation of useful cells having high safety and quality, while improving operability. A disposable set for cell culture includes a cell culture container (CC) having a liquid inlet (Lin) and a liquid outlet (Lout), a cell separation kit (A) that is for separating cells used for cell culture and is connected to the liquid inlet (Lin), and a cell collection kit (B) that is for washing and concentrating cultured cells in the cell culture container (CC) and is connected to the liquid outlet (Lout), and a cell culture device uses the disposable set for cell culture and includes flow path on-off valves and pumps provided at appropriate positions of pipelines of the disposable set and a controller controlling them.

18 Claims, 4 Drawing Sheets

(56) References Cited

U.S. PATENT DOCUMENTS

| | | | |
|---|---|---|---|
| 2003/0054335 A1 | | 3/2003 | Taya et al. |
| 2004/0259241 A1* | | 12/2004 | Barringer, Jr. ............ 435/309.2 |
| 2005/0064585 A1* | | 3/2005 | Wolf et al. ................ 435/297.4 |
| 2007/0157743 A1* | | 7/2007 | Jung .............................. 73/863 |
| 2008/0081367 A1* | | 4/2008 | Sowemimo-Coker et al. ............................ 435/325 |
| 2014/0193895 A1* | | 7/2014 | Smith et al. ................ 435/288.7 |
| 2014/0199713 A1* | | 7/2014 | Quake et al. ................ 435/7.21 |

OTHER PUBLICATIONS

Hellman et al., "Principles of Tissue Engineering," Published by NTS Inc., pp. 915-916.

Kenkyu-yo Kan'yo-kei Kansaibo Bunri Device, Catalog, Kaneka Corp., Feb. 2010.

Mackay et al., "Chondrogenic Differentiation of Cultured Human Mesenchymal Stem Cells from Marrow," Tissue Engineering, vol. 4, No. 4, 1998, pp. 414-428.

Pittenger et al., "Multilineage Potential of Adult Human Mesenchymal Stem Cells," Science, vol. 284, No. 5411, Apr. 2, 1999, pp. 143-147.

Poliard et al., "Controlled Conversion of an Immortalized Mesodermal Progenitor Cell Towards Osteogenic, Chondrogenic, or Adipogenic Pathways," The Journal of Cell Biology, vol. 130, No. 6, Sep. 1995, pp. 1461-1472.

Search Report issued in PCT/JP2011/065064, mailed on Sep. 27, 2011.

* cited by examiner

DISPOSABLE SET FOR CELL CULTURE, CELL CULTURE DEVICE AND CELL PREPARATION METHOD

TECHNICAL FIELD

The present invention relates to a disposable set for cell culture, a cell culture device, and a cell preparation method for sequentially carrying out all of a step of separating useful cells, a step of culturing the useful cells separated, and a step of washing and concentrating the cultured cells.

BACKGROUND ART

In recent years, a treatment in which cells are collected from body fluid or tissue of a patient or a donor, cultured to be amplified and processed, and transplanted to an affected area, so-called, regenerative medicine and cell medicine have been drawing attention. In the regenerative medicine and cell medicine, in many cases, useful cells to be used for a treatment are separated from a cell group collected from body fluid or tissue, and then the cells are amplified by culture. The cells obtained by culture are transplanted to, for example, a skin, a bone, a cartilage, or a cornea and are established to be safe and effective in some diseases of these organs. Therefore, such a medicine is expected to be generalized as a beneficial treatment method for patients (for example, see Non-Patent Document 1).

In recent years, it has been revealed that bone marrow fluid, cord blood, and others include adherent adult stem cells having characteristics of capable of being differentiated into various cells, such as bone cells, cartilage cells, muscle cells, and adipose cells (for example, see Non-Patent Documents 2 to 4). The adult stem cells can be differentiated into a wide variety of cells and organs. On this account, a method of efficiently separating and amplifying the adult stem cells is very important from a viewpoint of the development of regenerative medicine. At present, the adult stem cells are typically separated by a density gradient centrifugation method such as Ficoll-Paque fractionation (for example, see Non-Patent Document 5). However, the method requires a complicated procedure in which cells are repeatedly washed using a centrifuge for separating cells from a separation liquid. In addition, the method is accompanied by the risk of damage to cells due to the centrifugation or of contamination due to operation in an open system.

It was reported that the separated adult stem cells are present at a very small frequency of one in $10^4$ to $10^6$ nucleated cells in adult bone marrow fluid (for example, see Non-Patent Document 5). Hence, the separated adult stem cells are required to be cultured and amplified until the number of cells reaches a required value for treatment. At present, adult stem cells are typically amplified by culture using, for example, a petri dish, a flask, a culture bag, or a cartridge for culture in a $CO_2$ incubator at a temperature of 37° C. In this case, a culture medium exchange operation and a passage operation are carried out by an operator. Thus, each operation is accompanied with the risk of contamination and takes some time.

On this account, in recent years, automatic culture devices that automatically carry out culture operations such as seeding of cells and exchange of a culture medium and do not require labor have been developed (for example, see Patent Documents 1 to 3). However, current automatic culture devices have a single function of automatically culturing desired cells and do not have a function of separating desired cells from body fluid or tissue.

After amplifying intended cells until the number of cells reaches a predetermined value, the cells are treated with an enzyme such as trypsin or with a divalent cation chelating agent to be detached from a culture container and the detached cells are collected together with a liquid containing such an enzyme. Therefore, it is required to separately carry out an operation for removing the enzyme such as trypsin or the divalent cation chelating agent.

At present, a most common method of washing cells is centrifugation. In the method, cells are precipitated by centrifugation, a supernatant is removed, then a new washing liquid is added, the cells are re-suspended, and centrifugation is carried out once again. Such a procedure is repeated several times, thereby washing cells. However, for example, the procedure is complicated and a separate operation is not easy in a closed system. Therefore, the cell washing process is noted to involve the risk of contamination.

There is a method in which cultured cells are trapped using a separation material such as nonwoven fabric and the trapped cells are washed and then collected (for example, see Patent Document 4). However as with the centrifugation method, such a technique is used alone. Separation, culture, and collection of particular cells cannot be performed by a single device.

CITATION LIST

Patent Literatures

Patent Document 1: JP-A No. 2004-344128
Patent Document 2: JP-A No. 2004-089095
Patent Document 3: JP-A No. 2001-275659
Patent Document 4: JP-A No. 2008-086235

Non-Patent Literatures

Non-Patent Document 1: Robert Paul Lanza et al., translation supervisor: Tsuneya Ono et al, "Regenerative Medicine: Principles to most advanced technology of tissue engineering", published by NTS Inc., 2002

Non-Patent Document 2: Pliard A. et al., "Controlled Conversion of an Immortalized Mesodermal Progenitor Cell Towards Osteogenic, Chondrogenic, or Adipogenic Pathways.", J. Cell Biol. 130(6), pp. 1461-72, 1995

Non-Patent Document 3: Mackay A. M. et al., "Chondrogenic differentiation of cultured human mesenchymal Stem Cells from Marrow", Tissue Engineering, 4(4), pp. 414-428, 1998

Non-Patent Document 4: Angele P. et al., "Engineering of Osteochondoral Tissue with Bone Marrow Mesenchymal Progenitor Cells in a Derivatived Hyaluronan Geration Composite Sponge", Tissue Engineering 5(6), pp. 545-553, 1999

Non-Patent Document 5: Pittenger et al., "Multilineage Potential of Adult Human Mesenchymal Stem Cells", Science, Vol. 284, no. 5411, pp. 143-147, 1999

SUMMARY OF INVENTION

Technical Problem

As described above, for preparing cells useful for cell medicine or regenerative medicine, it is required to pass through a process (1) of separating useful cells to be seeded, a process (2) of culturing the useful cells separated, and a process (3) of washing and concentrating the cultured cells. At the present time, the culturing process (2) alone can be carried out with an automatic culture device and the other processes (1) and (3) are carried out as separate processes. Therefore, such a preparation procedure is noted to be complicated and to involve the risk of contamination.

In the method in which cells are trapped using a separation material such as nonwoven fabric and the cells are washed and then collected as in Patent Document 4, a cell collection liquid is passed in a direction opposite to the direction in which a cell suspension is passed, thereby collecting cells. Examples of means for pouring the cell collection liquid in this case include using a pump, crushing a bag storing the liquid, passing the liquid by drop, and manual pouring using a syringe or the like.

However, in order to collect trapped cells, also from the viewpoint of concentrating the cells, it is required to use a small amount of a cell collection liquid to collect the cells at once. The method using a syringe or a bag depends on manual operation and greatly varies in the collection ratio of cells. The method by drop greatly reduces the collection ratio of cells due to insufficient flow rate. The method using a pump also has problems as below. A syringe pump provides an insufficient flow rate, thereby collecting few cells. A roller pump provides a small flow rate at the time of start up due to its structure and a predetermined amount of a cell collection liquid flows before the liquid obtains a pressure needed for the collection of cells, resulting in a low collection ratio of cells.

Moreover, when collected cells are sent to a culture container at a pressure during the cell collection, as the next step of pouring a cell collection liquid, the cells are dashed to a culture face at a very high pressure. Hence, such a method causes large damage to the cells (for example, reduction in differentiation potential and in survivability). Therefore, the step also has many problems to be solved.

Therefore, in view of the above circumstances, an object of the present invention is to provide a disposable set for cell culture, a cell culture device, and a cell preparation method that sequentially carry out all of the step of separating useful cells, the step of culturing the useful cells separated, and the step of washing and concentrating the cultured cells, achieve a closed system having a simple structure without resorting to large scale equipment, and can prepare useful cells having high safety and quality while improving operability.

Solution to Problem

In order to solve the problems, a disposable set for cell culture of the present invention is characterized by including a cell culture container having a liquid inlet and a liquid outlet, a cell separation kit for separating cells used for cell culture, the cell separation kit being connected to the liquid inlet, and a cell collection kit for washing and concentrating cells cultured in the cell culture container, the cell collection kit being connected to the liquid outlet.

It is preferable that the cell separation kit include a cell separation material selectively trapping cells from a liquid to be treated containing the cells. It is preferable that the cell collection kit include a cell collection material trapping cultured cells and passing an impurity.

Also, it is preferable that the cell separation kit include a cell separation filter storing the cell separation material, the cell separation material selectively trapping cells from a liquid to be treated containing the cells, a tank for a liquid to be treated storing a liquid to be treated containing cells, the tank for a liquid to be treated being connected to an upstream side of the cell separation filter via a first pipeline, a drain tank connected to a downstream side of the cell separation filter via a second pipeline, a first cell collection liquid introduction part for introducing a cell collection liquid, the first cell collection liquid introduction part being connected by a pipeline branched at a midway point of the second pipeline, and a third pipeline branched at a midway point of the first pipeline and connected to the liquid inlet of the cell culture container.

Further, it is preferable that a cell storage bag for once storing cells collected by the cell collection liquid introduced from the first cell collection liquid introduction part to the cell separation filter be connected to a pipeline branched at a more upstream position of the first pipeline relative to the third pipeline.

Further, it is preferable that the tank for a liquid to be treated also serve as the cell storage bag once storing cells collected by the cell collection liquid introduced from the first cell collection liquid introduction part to the cell separation filter.

Also, it is preferable that the cell separation filter substantially trap cells useful for cell medicine or regenerative medicine by sending a liquid to be treated containing the cells useful for cell medicine or regenerative medicine and impurity cells to substantially pass the impurity cells through the cell separation filter, and the trapped cells be collected by passing the cell collection liquid in a direction opposite to the direction in which the liquid to be treated is passed.

Further, it is preferable that the first cell collection liquid introduction part be a syringe storing the cell collection liquid and a plunger of the syringe be pressurized by an external pressure unit driven by gas pressure to supply the cell collection liquid to the cell separation filter.

Further, it is preferable that a washing liquid tank storing a washing liquid be connected to an upstream side of the cell separation filter via a pipeline.

Also, it is preferable that at least one of a culture medium tank storing a culture medium and a cell detaching solution tank storing a cell detaching solution containing a cell detaching agent be connected by a pipeline branched at a midway point of the third pipeline.

Further, it is preferable that the cell collection kit include a cell collection filter storing the cell collection material, the cell collection material trapping cultured cells and passing an impurity, a fourth pipeline connected to the liquid outlet of the cell culture container and to an upstream side of the cell collection filter, a drain tank connected to a downstream side of the cell collection filter via a fifth pipeline, a second cell collection liquid introduction part for introducing a cell collection liquid, the second cell collection liquid introduction part being connected by a pipeline branched at a midway point of the fifth pipeline, and a cell collection tank for collecting cells collected by the cell collection liquid introduced from the second cell collection liquid introduction part to the cell collection filter, the cell collection tank being connected by a pipeline branched at a midway point of the fourth pipeline.

Further, it is preferable that a cell filter for removing a cell aggregate be interposed at a midway point of the fourth pipeline. It is preferable that a washing liquid tank storing a washing liquid be connected to an upstream side of the cell collection filter via a pipeline.

Also, it is preferable that the cell collection filter trap cultured cells by passing a cell suspension containing the cells cultured in the cell culture container and the trapped cells be collected by passing the cell collection liquid in a direction opposed to the direction in which the cell suspension is passed.

Further, it is preferable that the second cell collection liquid introduction part be a syringe storing the cell collection liquid and a plunger of the syringe be pressurized by an external pressure unit driven by gas pressure to supply the cell collection liquid to the cell collection filter.

In order to solve the problems, a cell culture device of the present invention uses the disposable set for cell culture and includes a flow path on-off valve for opening and closing a flow path by pinching the pipeline and a pump sequentially pressurizing the pipeline, the flow path on-off valve and the pump being provided at an appropriate position of the pipeline of the disposable set for cell culture, and a controller controlling opening and closing of the flow path on-off valve and controlling driving of the pump.

Also, in order to solve the problems, a cell culture device of the present invention uses the disposable set for cell culture in which the first cell collection liquid introduction part or the second cell collection liquid introduction part is a syringe storing the cell collection liquid and includes a flow path on-off valve for opening and closing a flow path by pinching the pipeline and a pump sequentially pressurizing the pipeline, the flow path on-off valve and the pump being provided at an appropriate position of the pipeline of the disposable set for cell culture, an external pressure unit pressurizing the plunger of the syringe, the external pressure unit being driven by compressed gas, and a controller controlling opening and closing of the flow path on-off valve, controlling driving of the pump, and controlling driving of the external pressure unit.

It is preferable that the compressed gas be supplied from a gas cylinder storing the compressed gas. It is more preferable that the compressed gas be carbon dioxide.

In order to solve the problems, a cell preparation method of the present invention uses the cell culture device and sequentially carries out a step of separating useful cells to be seeded, a step of culturing the useful cells separated in the separation step, and a step of washing and concentrating the cells cultured in the culturing step, in a closed system.

Advantageous Effects of Invention

As described above, the disposable set for cell culture, the cell culture device, and the cell preparation method of the present invention sequentially carry out all of the step of separating useful cells, the step of culturing the useful cells separated in the separation step, and the step of washing and concentrating the cells cultured in the culturing step, achieve a closed system having a simple structure without resorting to large scale equipment, and provide remarkable effect of capable of preparing useful cells having high safety and quality while improving operability.

In addition, a cell collection liquid is passed through the cell separation filter to collect cells and the cells are once stored in the tank for a liquid to be treated or the cell storage bag and then are transferred to the cell culture container. This eliminates the sending of the collected cells to the cell culture container at a pressure during the cell collection, thereby reducing damage to the cells due to high pressure during the cell collection.

Moreover, the first cell collection liquid introduction part or the second cell collection liquid introduction part is a syringe storing a cell collection liquid and a plunger of the syringe is pressurized by the external pressure unit driven by compressed gas. Thus, the cell collection liquid obtains a pressure needed for the collection of cells for a shorter period of time comparing with a common roller pump, thereby collecting the cells at once by a relatively small amount of the cell collection liquid. This improves the cell collection ratio and reduces the variation in the collection ratio.

BRIEF DESCRIPTION OF THE DRAWINGS

FIGS. 2(a) and 2(b) are longitudinal sectional views showing an example of driving of a cell collection liquid introduction part by an external pressure unit driven by compressed gas, in which FIG. 2(a) shows the state before driving, and FIG. 2(b) shows the completion state of the driving.

FIG. 4(a) shows Example 1, and FIG. 4(b) shows Reference Example 1.

DESCRIPTION OF EMBODIMENTS

Figure 1:
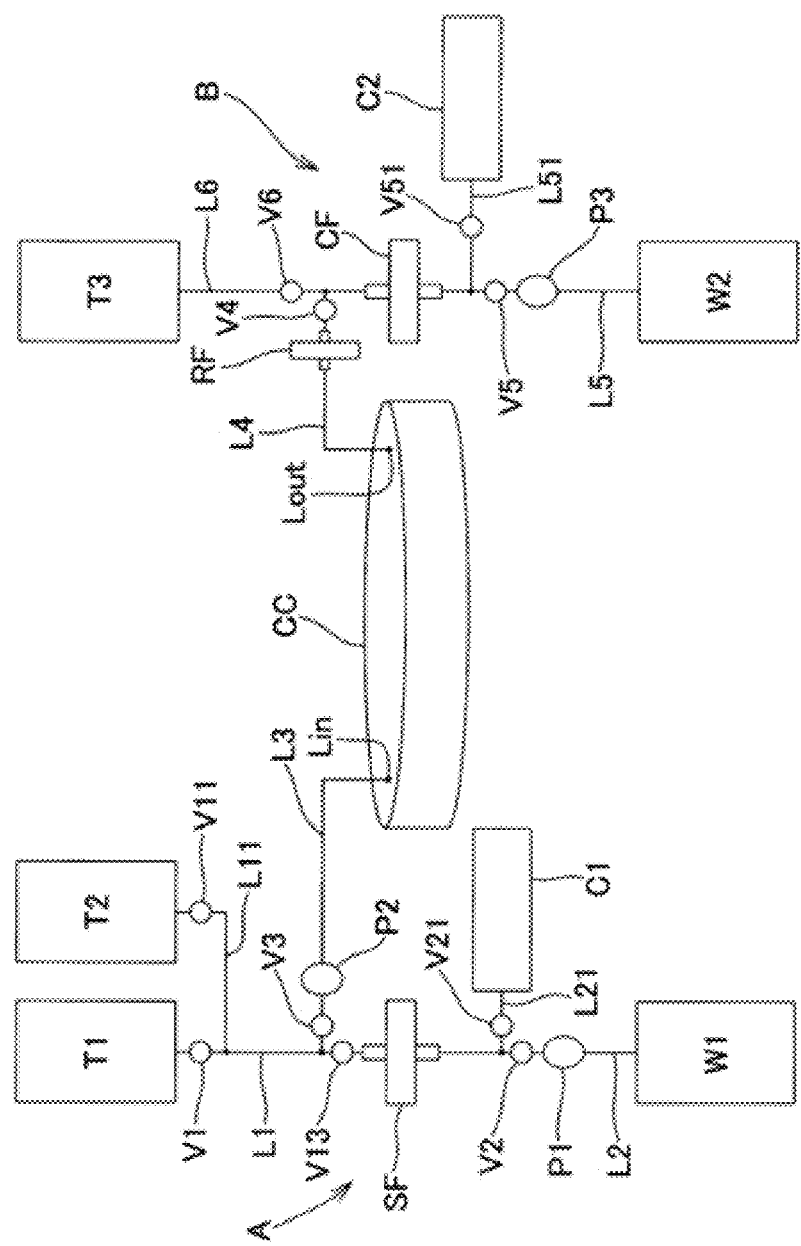
FIG. 1 is a schematic diagram showing a disposable set for cell culture and a cell culture device of a first embodiment in the present invention.

The present invention will now be specifically described.

In the present invention, a liquid to be treated containing cells may have any physical properties and chemical properties as long as the liquid contains cells. Specific examples of the liquid include, but are not limited to, body fluid such as bone marrow fluid, peripheral blood (including peripheral blood and G-CSF-mobilized peripheral blood), apheresis products (for example, a concentrated white blood cell solution), lymph, cord blood, menstrual blood, and semen; a treatment liquid obtained by separating cells by biochemical treatment of an organ, a tissue, or the like with a degradative enzyme such as collagenase or by physical treatment of an organ, a tissue, or the like with, for example, ultrasonic treatment, a homogenizer, or a sharp cutter; cells imparted with multipotency by gene recombination or other means of body cells, such as iPS cells; ES cells and others derived from fertilized embryos; and floating cells and spheroidal cells composed of cell aggregate.

The body fluid and the treatment liquid may be diluted with an appropriate liquid such as saline and a phosphate buffer solution before the treatment with a cell separation filter or may be concentrated by appropriate means such as centrifugation. Specific examples of the concentration method include, but are not limited to, a density gradient centrifugation method using, for example, Ficoll, Percoll, Lymphoprep, hydroxyethyl starch (HES), or Vacutainer tube.

In the present invention, an adult stem cell means a cell that is amplified to form a colony (cell group) when it is cultured in any condition except in a living body and has multipotency depending on various differentiation-inducing stimuli. Examples of the adult stem cell include, but are not limited to, a hematopoietic stem cell, an endothelial progenitor cell, and a mesenchymal stem cell.

In the present invention, a closed system means that an environment in a cell culture container of the present invention is isolated from an environment outside of the container and is not contaminated with bacteria and the like present in the outside environment. When a gas such as air and $CO_2$ is exchanged between inside and outside of the cell culture container, a filter having a pore size inhibiting the entry of bacteria is preferably provided, and the filter preferably has a pore size of, for example, 0.45 μm or 0.22 μm. In order to maintain the closed system, each part such as a bag, a tube, and various filters may be previously connected so as to form a closed system or parts isolated from each other may be connected immediately before use so as to maintain a closed system. The cell culture container of the present invention is preferably sterilized before use. Examples of the sterilization method include high pressure steam sterilization, ethylene oxide gas sterilization, gamma ray sterilization, and electron beam sterilization, but the present invention is not limited to them.

In the below description, a "pipeline" is a tube such as a polyvinyl chloride tube, a polyurethane tube, and a silicone tube, and an appropriate connector (joint) is used for a branched section or a joining section of the tubes.

In the below description, a "flow path on-off valve" is used for opening and closing a flow path of the tube by pinching the tube. Usable examples of the flow path on-off valve include a pinch valve and a roller valve.

In the below description, a "pump" is used for sending a liquid by sequentially pressurizing the tube with a roller or the like. Usable examples of the pump include a roller pump.

Opening and closing of the flow path on-off valve and the driving of the pump are controlled by a controller such as a programmable controller not shown in the drawings.

In the below description, each of a side of an inlet for a liquid to be treated with respect to a cell separation filter SF and a side of an inlet for a cell suspension with respect to a cell collection filter CF is referred to as an "upstream side", while a side of an outlet for a drain that is not trapped by the cell separation filter SF or the cell collection filter CF is referred to as a "downstream side".

First Embodiment

Hereinafter, a disposable set for cell culture and a cell culture device of a first embodiment in the present invention will be described with reference to a schematic diagram in FIG. 1.

The disposable set for cell culture includes a cell culture container CC having a liquid inlet Lin and a liquid outlet Lout, a cell separation kit A that is for separating cells to be used for cell culture and is connected to the liquid inlet Lin, and a cell collection kit B that is for washing and concentrating cells cultured in the cell culture container CC and is connected to the liquid outlet Lout. The components of the disposable set for cell culture are connected to form a closed system so as to aseptically carry out all of a step (1) of separating useful cells to be seeded, a step (2) of culturing the useful cells separated, and a step (3) of washing and concentrating the cultured cells. The disposable set for cell culture is discarded after use in order to improve safety.

[Cell Separation Kit]

The cell separation kit A is provided for separating cells to be used for cell culture. In the present embodiment, the cell separation kit A includes a cell separation filter SF, a tank T1 for a liquid to be treated, a cell storage bag T2, a drain tank W1, a first cell collection liquid introduction part C1, and others.

In other words, to an upstream side of the cell separation filter SF, the tank T1 for a liquid to be treated is connected via a pipeline L1 and the cell storage bag T2 is connected via a pipeline L11 branched at a midway point of the pipeline L1.

To a downstream side of the cell separation filter SF, the drain tank W1 is connected via a pipeline L2 and the first cell collection liquid introduction part C1 is connected via a pipeline L21 branched at a midway point of the pipeline L2.

A pipeline L3 branched at a midway point of the pipeline L1 and at a downstream side of the pipeline L11 is connected to the liquid inlet Lin of the cell culture container CC.

Here, the tank T1 for a liquid to be treated stores a liquid to be treated containing cells that are prepared by any method. In order to transfer the liquid to be treated in a closed system environment, the tank T1 for a liquid to be treated is preferably provided with an inlet that can be aseptically connected to preparation means of the liquid to be treated.

[Cell Separation Filter]

The cell separation filter SF has a function of selectively trapping cells from a liquid to be treated containing the cells. A cell separation material stored in the cell separation filter SF is characterized by that white blood cells and red blood cells in a liquid to be treated containing cells can be substantially passed through the material.

Here, the "substantially passing white blood cells and red blood cells in a liquid to be treated containing cells" means that, when a liquid to be treated containing cells is passed thorough the cell separation material, 30% or more of white blood cells and 80% or more of red blood cells in the liquid to be treated are not trapped by the cell separation material and are passed through the cell separation material.

From the viewpoint of separation performance of adult stem cells as intended cells, the cell separation material more preferably allows 45% or more of white blood cells and 85% or more of red blood cells in a liquid to be treated to be passed, the cell separation material even more preferably allows 60% or more of white blood cells and 90% or more of red blood cells in a liquid to be treated to be passed, and the cell separation material most preferably allows 70% or more of white blood cells and 95% or more of red blood cells in a liquid to be treated to be passed.

The cell separation material may have any physical properties, chemical properties, biochemical properties, and the like as long as the cell separation material achieves the passage ratio of white blood cells and red blood cells and can selectively trap adult stem cells. The shape, the opening size, the density, and the material of the cell separation material are specifically exemplified as below.

The shape of the cell separation material is not particularly limited but is preferably, for example, a porous material having a through hole structure, fiber aggregate, and fabric because such a shape is readily in contact with a liquid to be treated containing cells and has a large area to be in contact. The shape of the cell separation material is more preferably fiber and even more preferably nonwoven fabric as fiber aggregate.

A cell separation material composed of fiber or fiber aggregate preferably has a fiber diameter in a range from 3 to 40 µm from the viewpoint of the trapping and collection ratios of adult stem cells. A cell separation material composed of fiber having a fiber diameter of less than 3 µm reduces the passage ratio of impurity nucleated cells such as white blood cells, red blood cells, blood platelets, or the like, resulting in low removal efficiencies of them. A cell separation material composed of fiber having a fiber diameter of more than 40 µm reduces an effective contact area or readily causes short passes, thereby leading to the reduction in the trapping and collection ratios of adult stem cells. In order to increase the interaction between the adult stem cells and the cell separation material thereby to increase the yield, the fiber diameter is more preferably in a range from 5 to 35 µm and even more preferably in a range from 5 to 30 µm.

The cell separation material preferably has an opening size of 3 µm or more in minor axis and an opening size of 120 µm or less in major axis from the viewpoint of the trapping and collection ratios of adult stem cells. A cell separation material having an opening size of less than 3 µm in minor axis greatly reduces the removal efficiency of impurity nucleated cells such as white blood cells, red blood cells, and blood platelets. A cell separation material having an opening size of more than 120 µm in major axis makes the trapping of adult stem cells difficult.

From the viewpoint of, for example, the removal efficiency of impurity nucleated cells such as white blood cells, red blood cells, and blood platelets, the opening size is preferably 5 µm or more in minor axis and 80 µm or less in major axis. From the viewpoint of, for example, the removal efficiency of impurity nucleated cells such as white blood cells, red blood cells, and blood platelets and the trapping and collection ratios of adult stem cells, the opening size is more preferably 5 µm or more in minor axis and 70 µm or less in major axis. Here, the opening size is a mean value determined as follows. A cell separation material is observed under a scanning electron microscope to give a micrograph; a major diameter and a minor diameter of a substantial hole formed by the intersections of two or more different fibers are determined at fifty or more points with an image analyzer; and each mean value is calculated from the determined diameters.

The cell separation material preferably has a density in a range from $1.0\times10^4$ to $1.0\times10^6$ g/m$^3$ from the viewpoint of the removal efficiency of impurity nucleated cells such as white blood cells, red blood cells, and blood platelets and the trapping and collection ratios of adult stem cells. From the viewpoint of the removal efficiency of impurity nucleated cells such as white blood cells, red blood cells, and blood platelets, the density is more preferably in a range from $2.5\times10^4$ to $7.5\times10^5$ g/m$^3$ and even more preferably in a range from $5.0\times10^4$ to $5.0\times10^5$ g/m$^3$. Here, the density is a value obtained by dividing the weight (g) of a cell separation material by the volume (m$^3$).

The material of the cell separation material is preferably at least one material selected from polyolefins such as polypropylene, polyethylene, high-density polyethylene, and low-density polyethylene, polyester, polybutylene terephthalate, polyvinyl chloride, polyvinyl alcohol, polyvinylidene chloride, rayon, vinylon, polystyrene, acrylic polymers (such as polymethyl methacrylate, polyhydroxyethyl methacrylate, polyacrylonitrile, polyacrylic acid, and polyacrylic ester), nylon, polyurethane, polyimide, aramid, polyamide, cupra, Kevlar, carbon, polyacrylate, phenol, Tetron, pulp, hemp, cellulose, kenaf, chitin, chitosan, glass, cotton, and others. More preferably, the material is at least one synthetic or semisynthetic polymer selected from polyester, polypropylene, polystyrene, an acrylic polymer, rayon, polyolefin, vinylon, polyethylene, nylon, polyurethane, and others.

When two or more polymers are used in combination as the cell separation material, examples of the combination include, but are not necessarily limited to, a combination of polyester and polyolefin, a combination of rayon and polyolefin, and a combination of polyester, rayon, and vinylon. When two or more polymers are used in combination, a fiber form may be a fiber including a single fiber composed of polymers having different components to each other or a splittable fiber including different components split and divided to each other.

The fiber form may be a composite form including fibers each composed of a single polymer having a different composition. Here, the composite is not necessarily limited but examples of the composite include a form in which two or more fibers are mixed and a composite in which forms each composed of a single polymer are bonded to each other. However, the present invention is not limited to them.

In order to further improve the performance of the cell separation material, the material may be subjected to hydrophilic treatment. The hydrophilic treatment can improve performance. For example, non-specific trapping of cells except desired cells is suppressed and a body fluid is passed through the cell separation material without bias. The hydrophilic treatment can also improve the recovery efficiency of desired cells. Examples of the hydrophilic treatment method include a method of adsorbing a water-soluble polyhydric alcohol, a polymer having a hydroxy group, a cationic group, or an anionic group, or a copolymer thereof (for example, hydroxyethyl methacrylate, dimethylaminoethyl methacrylate, or a copolymer thereof), a method of adsorbing a water-soluble polymer substance such as polyethylene glycol, polyvinylpyrrolidone, and polyvinyl alcohol, a method of immobilizing a hydrophilic polymer to a hydrophobic membrane (for example, a method of chemically bonding a hydrophilic monomer to a surface), a method of applying electron beams to a cell separation material, a method of cross-linking and insolubilizing a hydrophilic polymer by applying radiation beams to a cell separation material containing water, a method of insolubilizing and immobilizing a hydrophilic polymer by heat treatment of a cell separation material in a dry condition, a method of treating a cell separation material with a component forming a water-insoluble composite together with a hydrophilic polymer, a sulfonation method of a surface of a hydrophobic membrane, a method of forming a membrane from a mixture of a hydrophilic polymer substance such as polyethylene glycol and polyvinylpyrrolidone and a hydrophobic polymer dope, a method of imparting a hydrophilic group to a membrane surface by treatment with an aqueous alkali (such as NaOH and KOH) solution, an insolubilization method in which a hydrophobic porous membrane is immersed in an alcohol, then is treated with an aqueous water-soluble polymer solution, and is dried, followed by heat treatment, treatment with radiation beams, or other treatments, and a method of adsorbing a substance having surface activity.

Examples of the substance having surface activity include nonionic surfactants, lecithin, polyoxyethylene hydrogenated castor oil, sodium edetate, sorbitan sesquioleate, D-sorbitol, dehydrocholic acid, glycerin, D-mannitol, tartaric acid, propylene glycol, macrogol, lanolin alcohol, and methyl cellulose. The nonionic surfactant is roughly classified into polyhydric alcohol fatty acid ester surfactants and polyoxyethylene surfactants. Examples of the polyhydric alcohol fatty acid ester surfactant include a glyceryl stearate surfactant, a sorbitan fatty acid ester, and a sorbitan acyl ester. Examples of the polyoxyethylene surfactant include polyoxyethylene alkyl ether, polyoxyethylene acyl ester, polyoxyethylene sorbitan acyl ester, polyoxyethylene sorbitan monolaurate, polyoxyethylene sorbitan monopalmitate, polyoxyethylene sorbitan monostearate, polyoxyethylene sorbitan tristearate, and polyoxyethylene sorbitan monooleate. These surfactants may be used alone or in combination. In order to improve adhesiveness of adult stem cells to the cell separation material, a cell adhesive protein or an antibody against an antigen expressed on adult stem cells may be immobilized on the cell separation material.

Examples of the cell adhesive protein include fibronectin, laminin, vitronectin, and collagen. Examples of the antibody include, but are not limited to, in the case that an intended cell is a mesenchymal stem cell, antibodies against CD73, CD90, CD105, and the like, in the case that an intended cell is a hematopoietic stem cell, antibodies against CD34, c-Kit, Sca-1, and the like, and in the case that an intended cell is a myoblast, antibodies against Myf5 and the like. Furthermore, for example, a surface may be subjected to hydrophilic treatment in order to be unlikely to cause cell adhesion, thereby performing surface modification, for example, cells are aggregated with each other to accelerate the formation of spheroids. A scaffold for supporting cells may also be provided in the cell culture container thereby to accelerate the formation of a composite of a cell and the scaffold, or a composite of a cell and a scaffold may be previously provided for culture.

The cell separation filter SF stores the cell separation material described above, but the shape, the size, the structural material, and others of the cell separation filter are not limited specifically.

The cell separation filter SF may have any shape, for example, a spherical shape, a container shape, a cassette shape, a bag shape, a tube shape, and a column shape. Specific examples of a preferred shape include a transparent or translucent column-shaped container having a volume of 0.5 to 1,000 ml and a diameter of 0.3 to 10 cm and a square pillar shape having 1 to 20-cm square or rectangular faces and having a thickness of 0.1 to 5 cm, but the present invention is not limited to them.

The cell separation filter SF can be prepared using any structural material. Specific examples of the material include a non-reactive polymer, a biocompatible metal, an alloy, and glass. Examples of the non-reactive polymer include an acrylonitrile polymer such as an acrylonitrile-butadiene-styrene terpolymer; a halogenated polymer such as polytetrafluoroethylene, polychlorotrifluoroethylene, a copolymer of tetrafluoroethylene and hexafluoropropylene, and polyvinyl chloride; and polyamide, polysulfone, polycarbonate, polyethylene, polypropylene, a polyvinyl chloride-acrylic copolymer, polycarbonate, acrylonitrile butadiene styrene, polystyrene, and polymethylpentene.

Examples of the metal material useful as the container material include stainless steel, titanium, platinum, tantalum, gold, an alloy of them, a gold plated ferroalloy, a platinum plated ferroalloy, a cobalt chromium alloy, and titanium nitride coated stainless steel. The container material is particularly preferably a material having sterilization resistance. Specific examples of the material include polypropylene, polyvinyl chloride, polyethylene, polyimide, polycarbonate, polysulfone, and polymethylpentene.

[Cell Separation Method Using Cell Separation Filter]

Next, a method for separating cells using the cell separation filter SF will be described.

A flow path on-off valve V11 on a pipeline L11, a flow path on-off valve V3 on a pipeline L3, and a flow path on-off valve V21 on a pipeline L21 are closed and flow path on-off valves V1 and V13 on a pipeline L1 and a flow path on-off valve V2 on a pipeline L2 are opened. Then, a pump P1 is driven to pass a liquid to be treated containing cells stored in a tank T1 for a liquid to be treated through a cell separation filter SF via the pipeline L1.

The flow rate of the liquid sent by the pump P1 is, for example, 0.1 to 100 ml/min, but the present invention is not limited to the flow rate. After the liquid to be treated containing cells is passed through the cell separation filter SF, the cell separation filter SF is preferably washed in order to remove impurity red blood cells and others. In this case, examples of a cell washing liquid include physiological saline, Ringer's solution, a culture medium used for cell culture, and a commonly used buffer solution such as a phosphate buffer solution. Among them, physiological saline is preferred from the viewpoint of safety. The cell washing liquid can be sent by the pump sending the liquid to be treated containing cells. In this case, the flow rate is, for example, 0.1 to 100 ml/min. The amount of the cell washing liquid varies depending on the volume of the cell separation filter SF but is preferably about 1 to 100 times the filter volume for washing.

[Method of Collecting Cells Trapped by Cell Separation Filter]

Most cells are present on an upstream side in the cell separation filter SF and thus a first cell collection liquid introduction part C1 is preferably disposed on a downstream side of the cell separation filter SF. From the first cell collection liquid introduction part C1, a cell collection liquid is passed through the cell separation filter SF in a direction opposed to the direction in which the liquid to be treated containing cells is passed, thereby collecting the cells.

In other words, the flow path on-off valves V1, V2, and V3 are closed and the flow path on-off valves V11, V13, and V21 are opened. Then, from the first cell collection liquid introduction part C1, the cell collection liquid is introduced, thereby storing the cells collected from the cell separation filter SF in a cell storage bag T2 via the pipelines L1 and L11.

Alternatively, the cell storage bag T2 in FIG. 1 may not be provided and the cells may be collected in the tank T1 for a liquid to be treated.

In this manner, the collected cells are collected in the cell storage bag T2 or the tank T1 for a liquid to be treated and the collected cells are not sent to a cell culture container CC at a pressure during the cell collection, thereby reducing damage to the cells due to high pressure during the cell collection.

The amount and the flow rate of the cell collection liquid vary depending on a filter volume. Preferably, 1 to 100 times the filter volume of the cell collection liquid is poured at 0.5 to 20 ml/sec, but the amount and the flow rate are not limited to them.

Figure 2:
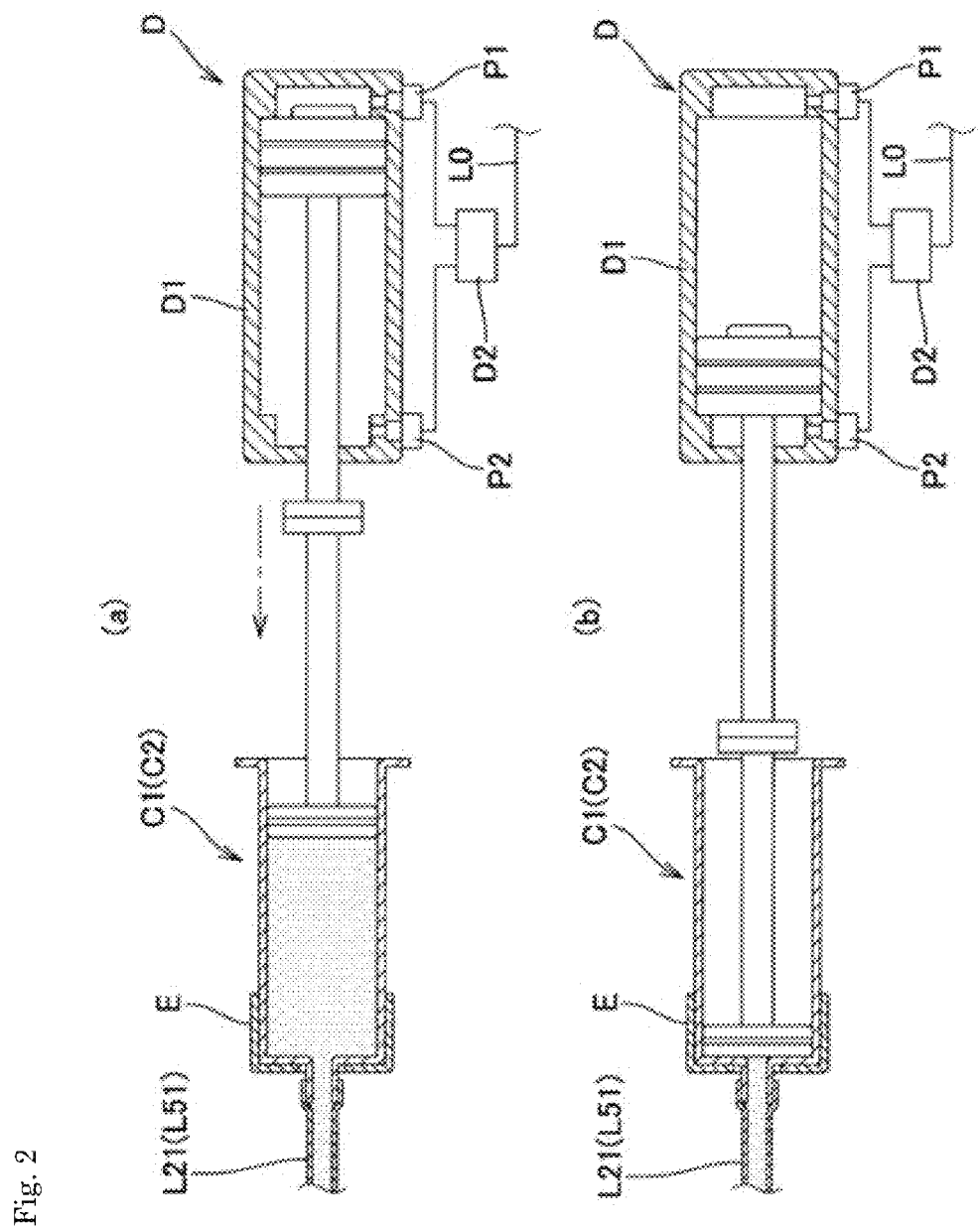

The cell collection liquid may be sent to the cell separation filter SF by a roller pump and the like, but is more preferably introduced using an external pressure unit D driven by compressed gas as shown in FIGS. 2(a) and 2(b). In other words, the first cell collection liquid introduction part C1 is composed of a syringe storing a cell collection liquid. An outer cylinder of the syringe is fixed to a holder E, and a plunger of the syringe is pushed by, for example, a piston rod of an air cylinder D1 as the external pressure unit D, thereby pushing out the cell collection liquid in the syringe into the pipeline L21 as shown in FIG. 2(a) and FIG. 2(b).

The air cylinder D1 can be driven by switching, with a flow path switching valve D2, ports P1 and P2 through which pressurized gas (examples of the gas include, but are not necessarily limited to, air, oxygen gas, nitrogen gas, and carbon dioxide gas, and carbon dioxide gas is preferred because carbon dioxide is used in a $CO_2$ incubator and others) is supplied from a pipeline L0. Such a driving is controlled by a controller such as a programmable controller not shown in the drawings.

In other words, a pressurized gas is supplied to the port P1 to thereby make the piston rod protrude as shown in FIG. 2(b), while a pressurized gas is supplied to the port P2 to thereby return the piston rod to the state in FIG. 2(a).

When a gas cylinder storing a pressurized gas is used as a supply source of the pressurized gas, the pressurized gas is easily supplied to the pipeline L0. Specifically, in a more preferred embodiment, a carbon dioxide gas cylinder is used as the supply source of a pressurized gas because the carbon dioxide gas cylinder is used for a $CO_2$ incubator and others and can be used easily.

The pressure for pressurizing the plunger of the syringe is preferably 0.05 MPa to 1 MPa. In order to improve the cell collection ratio and to reduce damage to cells, the pressure is more preferably 0.1 MPa to 0.75 MPa. From the viewpoint of a stable and high cell collection ratio and high expression of cell function, the pressure is even more preferably 0.2 MPa to 0.5 MPa.

Comparing with a common roller pump, the external pressure unit D driven by compressed gas makes the cell collection liquid obtain a pressure needed for the collection of cells in a shorter period of time, thereby collecting cells at once by a relatively small amount of the cell collection liquid. This improves the cell collection ratio and reduces the variation in the collection ratio.

The cell collection liquid is not particularly limited as long as the liquid is an isotonic solution. However, the cells collected from the cell separation filter SF are successively cultured in the cell culture container CC. Therefore, the cell collection liquid is preferably a liquid having a function capable of amplifying adult stem cells, namely, a culture medium for adult stem cells. In this case, specific examples of the culture medium for adult stem cells include, but are not limited to, a culture medium such as Dulbecco's Modified Eagle's Medium (D-MEM), Iscove's modified Eagle's medium (IMDM), RPMI1640 culture medium, MCDB133 culture medium, and ASF culture medium.

In order to increase the proliferative potential or the differentiation potential of collected stem cells, the culture medium may contain a biogenic substance such as serum and plasma; a protein factor such as basic fibroblast growth factor (bFGF), transforming growth factor-$\beta$ (TGF-$\beta$), insulin, transferrin, laminin, and fibronectin; and a low molecular substance such as retinoic acid, ascorbic acid, various amino acids, various sugars, 5-azacytidine, 2-mercaptoethanol, sodium selenite, hydrocortisone, and dexamethasone.

In order to avoid bacterial contamination during the culture process of stem cells, the liquid may contain antibiotics and antifungals such as kanamycin, gentamicin, penicillin, streptomycin, polymyxin B, vancomycin, and amphotericin B. Such a culture medium may also contain serum in an amount of 5 to 20%, as necessary.

[Cell Culture Container and Method for Culturing Collected Cells]

The flow path on-off valve V13 is closed, the flow path on-off valves V11 or V1 and V3 are opened, and the pump P2 is driven, thereby transferring the cell suspension stored in the cell storage bag T2 or the tank T1 for a liquid to be treated to the cell culture container CC via the pipelines L11, L1, and L3 or the pipelines L1 and L3.

The cell culture container CC may be any device and apparatus as long as adult stem cells contained in collected cells are cultured to amplify the number of the cells. A cell culture bag, a cell culture cassette, or a cell culture dish is preferably used due to easy handling and low possibility of risk of bacterial contamination and cross-contamination.

Examples of the material for such a structure include, but are not limited to, polystyrene, polyethylene terephthalate, vinyl chloride, polyethylene, polyolefin, an elastomer such as styrene-butadiene thermoplastic resin, polycarbonate, and polypropylene.

The cell culture container CC may have any shape, for example, a circular shape and a polygonal shape in a plan view. The shape is preferably a flat shape having a large bottom area in order to save space while culturing a large number of cells. In order to culture a large number of cells at a time, cell culture bags, cell culture cassettes, or cell culture dishes may be stacked to be used as a multistage structure or the inside of a container may be divided into multiple-stages, thereby culturing a large number of cells at a time. The number of cells to be seeded to the cell culture container CC varies depending on the type of cells. However, the number in a unit culture area is preferably $5 \times 10^2$ to $3 \times 10^4$ (cm$^2$). From the viewpoint of the proliferation capacity and the collection ratio of cells, the number is more preferably $1 \times 10^3$ to $1 \times 10^4$ (cm$^2$).

[Cell Collection Kit]

The cell collection kit B is for washing and concentrating cultured cells. In the present embodiment, the cell collection kit B includes a cell collection filter CF, a cell filter RF, a drain tank W2, a second cell collection liquid introduction part C2, a cell collection tank T3, and others.

In other words, a pipeline L4 connected to the liquid outlet Lout of the cell culture container CC is connected to an upstream side of the cell collection filter CF through the cell filter RF.

To a downstream side of the cell collection filter CF, the drain tank W2 is connected via a pipeline L5 and the second cell collection liquid introduction part C2 is connected via a pipeline L51 branched at a midway point of the pipeline L5.

To the upstream side of the cell collection filter CF, the cell collection tank T3 is connected via a pipeline L6 branched from the pipeline L4.

[Method of Detaching Cultured Cells from Cell Culture Container]

Next, a method of detaching cultured cells from the cell culture container CC will be described.

Cells cultured in the cell culture container CC for a predetermined period of time are detached, for example, by treatment with an enzyme such as trypsin or treatment with a chelating agent, and are introduced to the cell collection filter CF via the pipeline L4. At the time, some of the detached cells form aggregates. When the aggregates are sent to the cell collection filter without treatment, the filter may be clogged.

On this account, between the cell culture container CC and the cell collection filter CF, a cell filter RF having a pore size of 30 μm to 500 μm, more preferably 50 μm to 400 μm, is provided, thereby removing the cell aggregates. Then, the cell suspension is passed through the cell collection filter CF.

Cells are preferably treated with a cell detaching agent for about 1 to 15 minutes. The cell culture container CC may be shaken so that the cell detaching agent is evenly spread over the container.

If cells secreting a large amount of extracellular matrices, such as mesenchymal stem cells are cultured to a confluent state in which cells are spread, for example, all over a culture dish and cannot grow any further, the cells are unlikely to be collected as single cells by the treatment with a cell detaching agent. Consequently, the collection ratio may be lowered. In contrast, when the cells are collected at the initial stage of proliferation, the number of cells is likely to be small.

On this account, cells are preferably collected when the ratio of a cell occupying area with respect to a culturing area is 50% or more. The ratio is more preferably in a range from 70% to 90% for the reasons above, but the present invention is not limited to the range. All the cells detached by a cell detaching agent may be subjected to the next cell collection process or some of the cells may be left in the cell culture container to be sequentially cultured once again. The operation may be repeated several times, thereby increasing the number of cells.

[Cell Collection Filter]

The cell collection filter CF has a function of trapping cultured cells and passing impurities by a cell collection material stored in the cell collection filter CF. Examples of the impurity include cells except adult stem cells as the intended cells, solid substances such as cell membrane fragments, secretions derived from cells, a culture medium, and an enzyme such as trypsin and a chelating agent used for cell detachment, contained in the cell culture medium.

The material of the cell collection material is preferably at least one material selected from polyolefins such as polypropylene, polyethylene, high-density polyethylene, and low-density polyethylene, polyesters such as polyethylene terephthalate and polybutylene terephthalate, polyvinyl chloride, polyvinyl alcohol, polyvinylidene chloride, rayon, vinylon, polystyrene, acrylics (such as polymethyl methacrylate, polyhydroxyethyl methacrylate, acrylonitrile, acrylic acid, and acrylic ester), nylon, polyurethane, polyimide, aramid, polyamide, cupra, Kevlar, carbon, polyacrylate, phenol, Tetron, pulp, hemp, cellulose, kenaf, chitin, chitosan, glass, cotton, and others. The material is more preferably at least one synthetic polymer selected from polyester, polystyrene, acrylic, rayon, polyolefin, vinylon, polyethylene, nylon, polyurethane, and others.

When two or more synthetic polymers are used in combination as the cell collection material, examples of the combination include, but are not necessarily limited to, a combination of polyester and polyolefin, a combination of rayon and polyolefin, and a combination of polyester, rayon, and vinylon. When two or more synthetic polymers are used in combination, a fiber form may be a fiber including a single fiber composed of synthetic polymers having different components to each other or a splittable fiber including different components split and divided to each other. The fiber form may be a composite form including fibers each composed of a single synthetic polymer having a different composition. Here, the composite is not necessarily limited but examples of the composite include a form in which two or more fibers are mixed and a composite in which forms each composed of a single synthetic polymer are bonded to each other. However, the present invention is not limited to them. The shape of the cell collection material may be, for example, a porous material having a through hole structure, fiber aggregate, and fabric, but is more preferably nonwoven fabric.

The cell collection material preferably has a fiber diameter of 3 to 40 μm from the viewpoint of the collection ratio of adult stem cells. A cell collection material having a fiber diameter of less than 3 μm increases the interaction with white blood cells, thereby reducing the removal efficiency of unnecessary cells. A cell collection material having a fiber diameter of more than 40 μm readily reduces an effective contact area or readily causes short passes, thereby leading to the reduction in the collection ratio of adult stem cells. In order to increase the interaction between adult stem cells and the filter thereby to increase the yield, the fiber diameter is more preferably 5 to 35 μm. Even more preferably, the fiber diameter is 5 μm to 30 μm.

The cell collection material preferably has an opening size of 3 μm or more in minor axis and an opening size of 120 μm or less in major axis from the viewpoint of the trapping performance of adult stem cells. A cell collection material having an opening size of less than 3 μm in minor axis may reduce the removal efficiency of impurities. A cell collection material having an opening size of more than 120 μm in major axis makes the trapping of adult stem cells difficult.

From the viewpoint of the removal efficiency of comparatively large impurities such as red blood cells, the cell collection material more preferably has an opening size of 5 to 80 μm. From the viewpoint of the trapping performance of adult stem cells, the opening size is even more preferably 5 to 30 μm. Here, the opening size is a mean value determined as follows. A cell collection material is observed under a scanning electron microscope to give a micrograph; a major diameter and a minor diameter of a substantial hole formed by the intersections of two or more different fibers are determined at fifty or more points with an image analyzer; and each mean value is calculated from the determined diameters.

The cell collection filter CF may have any shape, for example, a spherical shape, a container shape, a cassette shape, a bag shape, a tube shape, and a column shape. Specific examples of a preferred shape include a transparent or translucent column-shaped container having a volume of 0.1 to 1,000 ml and a diameter of 0.3 to 15 cm and a square pillar shape having 0.1 to 20-cm square or rectangular faces and a thickness of 0.1 to 5 cm.

The cell collection filter CF may have a plate shape cut into an appropriate size for treating a body fluid or may have a rolled-up shape for treating a body fluid. When the rolled-up filter is used, a body fluid may be treated from the inside to the outside of the roll, thereby trapping desired cells, or in reverse, a body fluid may flow from the outside to the inside of the roll, thereby trapping adult stem cells. Specific examples have been described in the above, but the present invention is not limited to them.

[Method of Washing and Concentrating Cultured Cells Using Cell Collection Filter]

Next, a method of washing and concentrating cultured cells using the cell collection filter CF will be described.

A flow path on-off valve V6 on the pipeline L6 and a flow path on-off valve V51 on a pipeline L51 are closed, a flow path on-off valve V4 on the pipeline L4 and a flow path on-off valve V5 on a pipeline L5 are opened, and a pump P3 is driven, thereby sending a cell suspension containing, for example, an enzyme such as trypsin or a chelating agent that is used in order to detach cells cultured for a predetermined period of time, from the cell culture container CC to the cell collection filter CF via the pipeline L4.

After the cell suspension containing, for example, an enzyme such as trypsin or a chelating agent is passed through the cell collection filter CF, the cell collection filter is preferably washed in order to remove an enzyme such as trypsin and a chelating agent remaining in the filter.

In this case, examples of a cell washing liquid include physiological saline, Ringer's solution, a culture medium used for cell culture, and a commonly used buffer solution such as a phosphate buffer solution. The cell washing liquid can be sent by the pump sending the cell suspension containing, for example, an enzyme such as trypsin or a chelating agent. In this case, the flow rate is, for example, 0.1 to 100 ml/min. The amount of the cell washing liquid varies depending on the volume of the cell collection filter CF, but is preferably about 1 to 100 times the filter volume for washing.

Most cells are present on an upstream side in the cell collection filter CF and thus a second cell collection liquid introduction part C2 is preferably disposed on a downstream side of the cell collection filter CF. From the second cell collection liquid introduction part C2, a cell collection liquid is passed through the cell collection filter CF in a direction opposed to the direction in which the cell suspension is passed, thereby collecting the cells.

In other words, the flow path on-off valves V4 and V5 are closed and the flow path on-off valve V6 and V51 are opened. Then, the cell collection liquid is introduced from the second cell collection liquid introduction part C2. As a result, the cells collected from the cell collection filter CF are stored in a cell collection tank T3 via the pipelines L4 and L6, thereby obtaining the cells as a final product.

The cell collection tank T3 may be any device and is preferably a bag, a test tube, a tube, or others because such a device is easily carried and has low risk of bacterial contamination and cross-contamination. Examples of the material for such a structure include, but are not limited to, polystyrene, polyethylene terephthalate, vinyl chloride, polyethylene, polyolefin, an elastomer such as styrene-butadiene thermoplastic resin, polycarbonate, and polypropylene.

The amount and the flow rate of the cell collection liquid vary depending on a filter volume. Preferably, 1 to 50 times the filter volume of the cell collection liquid is poured at 0.5 to 20 ml/sec but the amount and the flow rate are not limited to them.

The cell collection liquid is not particularly limited as long as the liquid is an isotonic solution. However, the cells collected from the cell collection filter CF are used for, for example, transplant. Therefore, preferred examples of the cell collection liquid include a liquid actually used for medical purposes, such as physiological saline and Ringer's solution, plasma, serum, and a solution of physiological saline or Ringer's solution containing albumin, plasma, or serum.

The cell collection liquid may be introduced to the cell collection filter CF by a roller pump and the like, but is more preferably introduced using an external pressure unit D driven by compressed gas as shown in FIGS. 2(a) and 2(b). In other words, the second cell collection liquid introduction part C2 is composed of a syringe storing a cell collection liquid. An outer cylinder of the syringe is fixed to a holder E and a plunger of the syringe is pushed by, for example, a piston rod of an air cylinder D1 as the external pressure unit D, thereby pushing out the cell collection liquid in the syringe into the pipeline L51 as shown in FIG. 2(a) and FIG. 2(b).

The air cylinder D1 can be driven by switching, with a flow path switching valve D2, ports P1 and P2 through which pressurized gas (examples of the gas include, but are not necessarily limited to, air, oxygen gas, nitrogen gas, and carbon dioxide gas, and carbon dioxide gas is preferred because carbon dioxide is used in a $CO_2$ incubator and others) is supplied from a pipeline L0. Such a driving is controlled by a controller such as a programmable controller not shown in the drawings.

In other words, pressurized gas is supplied to the port P1 to thereby make the piston rod protrude as shown in FIG. 2(b), while a pressurized gas is supplied to the port P2 to thereby return the piston rod to the state in FIG. 2(a).

The pressure for pressurizing the plunger of the syringe is preferably 0.05 MPa to 1 MPa. In order to improve the cell collection ratio and to reduce damage to cells, the pressure is more preferably 0.1 MPa to 0.75 MPa. From the viewpoint of a stable and high cell collection ratio and high expression of cell function, the pressure is even more preferably 0.2 MPa to 0.5 MPa.

Comparing with a common roller pump, the external pressure unit D driven by compressed gas makes the cell collection liquid obtain a pressure needed for the collection of cells in a shorter period of time, thereby collecting cells at once by a relatively small amount of the cell collection liquid. This improves the cell collection ratio and reduces the variation in the collection ratio.

Second Embodiment

Next, a disposable set for cell culture and a cell culture device of a second embodiment in the present invention will be described with reference to a schematic diagram of FIG. 3. The same signs in FIG. 3 as those in FIG. 1 show the same parts or corresponding parts. Thus, in the following description, those with the same signs as in FIG. 1 may not be described in detail.

The present embodiment shows a more preferred method in which adult stem cells are separated from a liquid to be treated containing the adult stem cells with a cell separation filter SF, then the separated cells are cultured in a cell culture container CC, and the cells are washed with a cell collection filter CF to remove an enzyme, a chelating agent, and the like, thereby collecting the concentrated cells.

[Cell Separation Kit]

A cell separation kit A of the second embodiment does not include the cell collection bag T2 of the first embodiment and the tank T1 for a liquid to be treated is also used for cell collection. In addition to the cell separation kit A of the first embodiment, a washing liquid tank WA1 is connected via a pipeline L12 branched at a midway point of the pipeline L1, a culture medium tank T4 is connected via a pipeline L31 branched at a midway point of the pipeline L3, and a cell detaching solution tank T5 is connected via a pipeline L32 branched at a midway point of the pipeline L31.

[Cell Collection Kit]

In a cell collection kit B of the second embodiment, in addition to the cell collection kit B of the first embodiment, a drain tank W3 is connected to the liquid outlet Lout of the cell culture container CC via a pipeline L7 and a washing liquid tank WA2 is connected via a pipeline L8 branched at a midway point of the pipeline L6.

A pump P1 is driven in the same manner as in the first embodiment to pass a liquid to be treated containing adult stem cells stored in the tank T1 for a liquid to be treated through the cell separation filter SF via the pipeline L1.

The passing rate of a liquid to be treated through the cell separation filter SF is not particularly limited but is preferably in a range from 0.1 to 1,000 mm/min in terms of passing velocity (linear velocity) of a liquid to be treated with respect to the thickness of a cell separation material. A liquid to be treated having a linear velocity of less than 0.1 mm/min elongates the treatment time, while a liquid to be treated having a linear velocity of more than 1,000 mm/min makes trapping of adult stem cells by the separation material difficult due to running pressure of the liquid to be treated. The linear velocity is more preferably 0.5 to 500 mm/min and even more preferably 1 to 250 mm/min.

When the cell separation filter SF is washed with an isotonic solution such as physiological saline before the liquid to be treated containing adult stem cells is passed through the cell separation filter SF, flow path on-off valves V1, V3, and V21 are closed, a flow path on-off valve V2 and a flow path on-off valve V12 on the pipeline L12 are opened, and the pump P1 is driven. As a result, the washing liquid such as physiological saline stored in the washing liquid tank WA1 is passed through the cell separation filter SF via the pipeline L12 and the pipeline L1 and a drain is stored in a drain tank W1 via a pipeline L2. The linear velocity at this time is not particularly limited but is preferably in a range from 0.1 to 1,000 mm/min.

By passing the liquid to be treated containing adult stem cells through the cell separation filter SF, the adult stem cells in the liquid to be treated are trapped by the cell separation material and unnecessary components that are not trapped, such as red blood cells, nucleated cells except adult stem cells, plasma components, enzymes, a buffer solution used for dilution are transferred to the drain tank W1 via the pipeline L2.

By passing the liquid to be treated containing adult stem cells through the cell separation filter SF, the adult stem cells are trapped by the cell separation material. However, some red blood cells and nucleated cells may remain in the cell separation material together with the adult stem cells. In order to remove these unnecessary cells, a washing liquid may be passed through the cell separation filter SF from the washing liquid tank WA1 via the pipeline L12 and the pipeline L1. In this case, an inlet of the washing liquid is preferably provided at the same position as an inlet of the liquid to be treated that is passed through the cell separation filter SF or at an upstream side of the inlet.

The washing liquid used here is not particularly limited as long as the liquid does not adversely affect adult stem cells. Specific examples of the washing liquid include physiological saline, Ringer's solution, serum, plasma, a culture medium used for cell culture, and a common buffer solution such as a phosphate buffer solution. Physiological saline is preferably used because it has small adverse effect on adult stem cells and is actually used for medical purposes. In any case, the washing liquid is preferably passed through in a similar condition to the condition in which the liquid to be treated is passed through the cell separation filter SF.

By passing the washing liquid through the cell separation filter SF, unnecessary cells except adult stem cells remaining in the cell separation filter SF are transferred from the cell separation filter SF to the drain tank W1 via the pipeline L2 together with the washing liquid.

By passing a cell collection liquid through the cell separation filter SF from a first cell collection liquid introduction part C1 via a pipeline L21, the adult stem cells trapped by the cell separation filter SF are once stored in the tank T1 for a liquid to be treated via the pipeline L1, then are transferred to the cell culture container CC via the pipelines L1 and L3, and are cultured without treatment.

At this time, a liquid having a function capable of growing stem cells, such as a culture medium for culturing stem cells is preferably used as the cell collection liquid because the cells can be cultured after transfer without treatment.

Most adult stem cells are present on the upstream side in the cell separation filter SF and thus the pipeline L21 is preferably connected to the pipeline L2 provided at a downstream side of the cell separation filter SF.

As necessary, the flow path on-off valve V3 on the pipeline L3 is closed, a flow path on-off valve V31 on the pipeline L31 is opened, and a pump P2 is driven, thereby adding a culture medium to the cell culture container CC from the culture medium tank T4 filled with a culture medium via the pipelines L31 and L3.

The adult stem cells collected from the cell separation filter SF are cultured using the cell culture container CC and are amplified until the number of cells reaches a required value. At this time, the cells may be amplified while maintaining characteristics as the adult stem cells or may be induced and differentiated into appropriate particular cells or tissues. Both a cell composition amplified while maintaining characteristics as adult stem cells and a cell composition induced and differentiated into particular cells or tissues are included in the present invention. After the adult stem cells are amplified in the cell culture container CC until the number of cells reaches a required value, some of the cells may be left and sequentially cultured in the cell culture container CC.

For detaching the cells grown in the cell culture container CC, a pump P4 is driven to drain the culture medium to the drain tank W3 via the pipeline L7.

When a culture medium remains in the cell culture container CC, a cell detaching agent may not effectively work due to the effect of a protein component, divalent cations, and others in the culture medium. On this account, the pump P2 may be driven and a washing liquid in the washing liquid tank WA1 may be poured into the cell culture container CC via the pipeline L12 and the pipeline L3, thereby washing the remaining culture medium.

When the washing is carried out, the pump P4 is driven to drain the washing liquid to the drain tank W3 via the pipeline L7.

Next, the pump P2 is driven and a cell detaching agent for detaching cells, for example, an enzyme such as trypsin and a chelating agent in the cell detaching solution tank T5 is poured into the cell culture container CC via the pipelines L32, L31, and L3. At the time, the cell culture container CC may be shaken so that the cell detaching agent is evenly spread over the cell culture container CC.

Cells are preferably treated with a cell detaching agent for about 1 to 15 minutes. After a predetermined period of time, a culture medium is added from the culture medium tank T4 via the pipelines L31 and L3 in order to inactivate the cell detaching agent. Before a cell culture medium is added, the cell culture container CC containing the cell detaching agent may be shaken in order to thoroughly detach cells.

The cell suspension in which the cell detaching agent and the culture medium are mixed is passed through a cell filter RF from a pipeline L4 and passed through the cell collection filter CF, thereby trapping the grown cells by the cell collection filter CF.

Unnecessary components such as nucleated cells except the trapped cells, serum components, enzymes, a chelating agent, and a culture medium are transferred to a drain tank W2 via a pipeline L5.

An enzyme such as trypsin, a chelating agent, or the like used for cell detachment may remain in the cell collection filter CF. Thus, in order to remove such an unnecessary component, a washing liquid such as physiological saline in the washing liquid tank WA2 may be passed through the cell collection filter CF via the pipelines L8, L6, and L4.

The passing rate of a liquid to be treated through the cell collection filter CF and the flow rate for washing the cell collection filter CF are not particularly limited but are preferably in a range from 0.1 to 1,000 mm/min in terms of passing velocity (linear velocity) of a liquid to be treated with respect to the thickness of a filter. The linear velocity is more preferably 0.5 to 500 mm/min and even more preferably 1 to 250 mm/min.

The washing liquid used here is not particularly limited as long as the liquid does not adversely affect cells. Specific examples of the washing liquid include a liquid actually used for injection, such as physiological saline and Ringer's solution.

The amount of the cell washing liquid varies depending on the volume of the cell collection filter CF but is preferably about 1 to 100 times the filter volume for washing.

The cells trapped by the cell collection filter CF can be collected by passing the cell collection liquid in a direction opposite to the direction in which the cell suspension is passed. Specifically, a cell collection liquid is passed through the cell collection filter CF from a second cell collection liquid introduction part C2 via a pipeline L51 and the pipeline L5, thereby collecting the cells into a cell collection tank T3 via the pipelines L4 and L6.

Most cells are present on an upstream side in the cell collection filter CF and thus the pipeline L51 is preferably connected to the pipeline L5 provided at a downstream side of the cell collection filter CF. The cell collection liquid is not particularly limited as long as the liquid does not adversely affect cells. Specific examples of the cell collection liquid include a liquid actually used for injection, such as physiological saline and Ringer's solution, as well as plasma and serum. Plasma, serum, and the like may be added to physiological saline, Ringer's solution, or the like to be used.

Example 1

Figure 3:
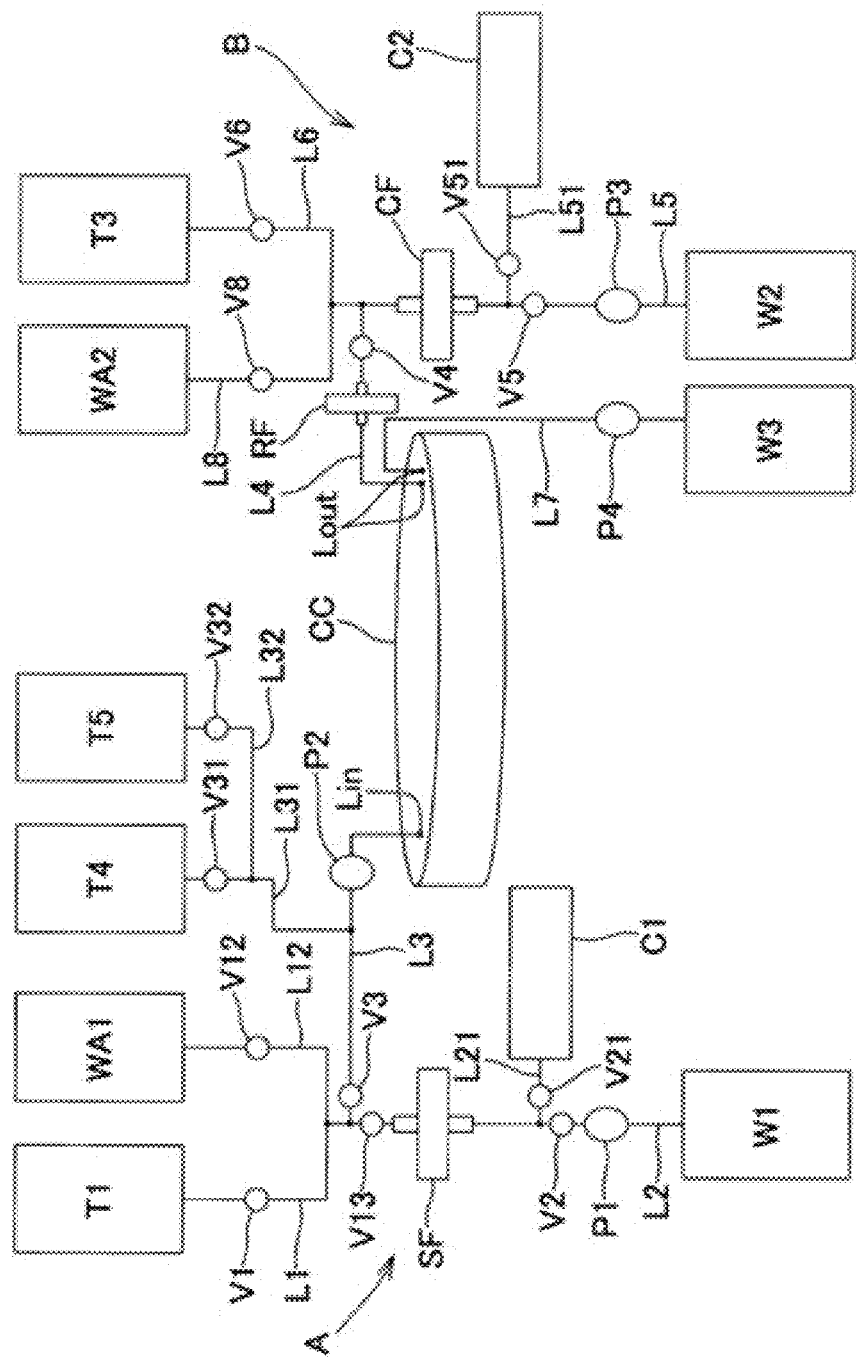
FIG. 3 is a schematic diagram showing a disposable set for cell culture and a cell culture device of a second embodiment in the present invention.

The used cell culture device included a disposable set for cell culture in FIG. 3. The disposable set for cell culture includes a cell culture container CC, a cell separation kit A, and a cell collection kit B. The used cell culture device was provided with flow path on-off valves and pumps at positions shown in FIG. 3 and was equipped with a controller that controlled opening and closing of the flow path on-off valves, controlled driving of the pumps, and controlled driving of an external pressure unit D shown in FIG. 2.

As a cell separation filter SF, a cylindrical-shaped column provided with an inlet and an outlet and having an outer diameter of 26 mm and an inner diameter of 22 mm was used. The column stored a cell separation material that was prepared by compressing stacked 36 pieces of nonwoven fabric (density (basis weight $(g/m^2)$/thickness (m))=$1.8 \times 10^5$ (95/($5.2 \times 10^{-4}$)) $(g/m^3)$, fiber diameter=$15 \pm 10$ μm, opening size=5 to 50 μm) made of polyester and propylene until the thickness of the nonwoven fabric reached 9 mm.

First, 30 ml of physiological saline in a washing liquid tank WA1 was passed through the cell separation filter SF via pipelines L12 and L1 at a flow rate of 30 ml/min, thereby washing the filter.

Next, 20 ml of purchased human bone marrow fluid was charged in a tank T1 for a liquid to be treated. The human bone marrow fluid in the tank T1 for a liquid to be treated was introduced to the cell separation filter SF via the pipeline L1 at a flow rate of 6 ml/min. A sample of the liquid to be treated passed through the cell separation filter SF was collected from a pipeline L2. The number of blood cells in the collected sample was counted with an automatic hematology analyzer (Sysmex K-4500).

Next, 30 ml of physiological saline in the washing liquid tank WA1 was passed through the cell separation filter SF via the pipelines L12 and L1 at a flow rate of 6 ml/min, thereby washing and removing red blood cells, white blood cells, and blood platelets.

Next, as a cell collection liquid, 150 ml of cell culture medium (α-MEM medium (manufactured by GIBCO)) containing 10% fetal bovine serum was stored in a syringe as a first cell collection liquid introduction part C1. Then, a plunger of the syringe was pressurized by the external pressure unit D shown in FIG. 2 using carbon dioxide as a compressed gas and the cell collection liquid was poured at a flow rate of 300 ml/min and a pressure of 0.3 MPa from the first cell collection liquid introduction part C1 to the cell separation filter SF via a pipeline L21 and the pipeline L2 in a direction opposed to the direction in which the bone marrow fluid is passed, thereby once storing an intended cell fraction in the tank T1 for a liquid to be treated from the cell separation filter SF via the pipeline L1.

Next, the cell fraction was transferred to the cell culture container CC (diameter 250 mm) via the pipeline L1 and a pipeline L3 and a sample was collected from the pipeline L3. The number of blood cells in the collected sample was counted with an automatic hematology analyzer (Sysmex K-4500).

The number of blood cells after passing through the cell separation filter SF was divided by the number of blood cells before passing to determine the passage ratio of blood cells. Each passage ratio of red blood cells and blood platelets was 95% or more and the passage ratio of white blood cells was 70%.

The number of cells in the collected solution was divided by the number of blood cells before passing through the cell separation filter SF to determine the cell collection ratio. As shown in Table 1, the collection ratio of red blood cell was 0.5%, the collection ratio of blood platelet was 4%, and the collection ratio of white blood cell was 25%.

The above result reveals that most of red blood cells and blood platelets were removed by the cell separation filter SF.

TABLE 1

|  | Collection ratio of red blood cell (%) | Collection ratio of white blood cell (%) | Collection ratio of blood platelet (%) |
|---|---|---|---|
| Example 1 | 0.5 | 25 | 4 |
| Comparative Example 1 | less than 1 | 25 | 9 |

The cell collection liquid containing the cell fraction transferred to the cell culture container CC was cultured in a 5% $CO_2$ incubator at a temperature of 37° C. for 14 days. During the culture, the culture medium was exchanged every two or three days and the cells were grown until the bottom area of the cell culture container CC reached almost confluent.

Next, a washing and concentrating method after mesenchymal stem cells derived from human bone marrow fluid were cultured will be described.

As a cell collection filter CF, a cylindrical-shaped column provided with an inlet and an outlet and having an outer diameter of 26 mm and an inner diameter of 22 mm was used. The column stored a cell collection material that was prepared by compressing stacked 36 pieces of nonwoven fabric (density (basis weight $(g/m^2)$/thickness (m))=$1.6 \times 10^5$ (85/($5.3 \times 10^{-4}$)) $(g/m^3)$, fiber diameter=$12 \pm 2$ μm, opening size=10 to 26 μm) made of polyester until the thickness of the nonwoven fabric reached 9 mm.

First, 30 ml of physiological saline in a washing liquid tank WA2 was passed through the cell collection filter CF via a pipeline L8 at a flow rate of 30 ml/min, thereby washing the filter.

Next, the cell culture medium was drained to a drain tank W3 via a pipeline L7 and 100 ml of physiological saline in the washing liquid tank WA2 was poured into the cell culture container CC via the pipeline L8 and pipelines L6 and L4.

Next, the physiological saline in the cell culture container CC was drained into the drain tank W3 via the pipeline L7, thereby washing the inside of the cell culture container CC.

Next, 75 ml of trypsin-EDTA solution (TrypLE Select, manufactured by GIBCO) in a cell detaching solution tank T5 was added into the cell culture container CC from which the physiological saline was removed via pipelines L32 and L31 and the pipeline L3, and the cell culture container CC was shaken. Then, the cell culture container CC was allowed to stand at a temperature of 37° C. for 10 minutes, and the cell culture container CC was shaken once again, thereby detaching the cells.

Next, 150 ml of cell culture medium in a culture medium tank T4 was added into the cell culture container CC via the pipelines L31 and L3, thereby preparing a cell suspension containing cultured cells that were detached.

The cell suspension was passed through a cell filter RF (70 μm) via the pipeline L4 and passed through the cell collection filter CF at a flow rate of 10 ml/min and a drain passed through the cell collection filter CF was drained into a drain tank W2 via a pipeline L5.

A sample of the cell suspension that was introduced to the cell collection filter CF and was passed through the cell collection filter CF was collected from the pipeline L5.

Next, 30 ml of physiological saline in the washing liquid tank WA2 was passed through the cell collection filter CF via the pipeline L8 at a flow rate of 10 ml/min thereby to remove the cell detaching agent such as trypsin used for the cell detachment from the cells trapped by the cell collection filter CF.

Next, as a cell collection liquid, 10 ml of serum was stored in a syringe as a second cell collection liquid introduction part C2. Then, a plunger of the syringe was pressurized by the external pressure unit D shown in FIG. 2 using carbon dioxide as a compressed gas and the cell collection liquid was poured at a flow rate of 300 ml/min and a pressure of 0.3 MPa from the second cell collection liquid introduction part C2 to the cell collection filter CF via a pipeline L51 and the pipeline L5 in a direction opposed to the direction in which the cell suspension is passed, thereby collecting the cells after washing into a cell collection tank T3 from the cell collection filter CF via the pipeline L6.

The number of cells after passing through the cell collection filter CF was divided by the number of cells before passing through the cell collection filter CF to determine the passage ratio of the cultured cell through the cell collection filter CF.

The number of cultured cells collected in the cell collection tank T3 was divided by the number of cells before passing through the cell collection filter CF to determine the cell collection ratio from the cell collection filter CF.

The number of cells was determined with a hemocytometer.

As a result, as shown in Table 2, the number of cells after culture for 14 days was as very high as $2.0 \times 10^7$.

The number of cells was 2.5 times higher than that obtained by converting the number of cells from bone marrow fluid (2 ml) treated in Comparative Example 1 described later (typically employed stem cell separation method) into the number of cells from the fluid (20 ml) treated with the cell separation filter SF.

The number of cells when the cell suspension was treated with the cell collection filter CF was below the detection limit of the hemocytometer and the cell passage ratio was 0%. Almost all cells were trapped by the cell collection filter CF. At this time, the number of cells collected from the cell collection filter CF was $1.8 \times 10^7$ as shown in Table 2 and the collection ratio was as very high as 90%.

Here, the amount of the cell suspension containing a trypsin solution was reduced from 225 ml to 10 ml and it was ascertained that the cells were concentrated.

The final trypsin concentration in the physiological saline from the outlet of the cell collection filter CF when the cell suspension was passed through the cell collection filter CF and then the cell collection filter CF was washed with physiological saline was below the detection limit at 280 nm in an ultraviolet absorption spectra, as shown in Table 2. Trypsin was thoroughly washed and removed.

TABLE 2

|  |  | The number of cells after culture for 14 days | Remaining trypsin ratio (%, with respect to treatment concentration[note 1]) |
|---|---|---|---|
| Example 1 | Before cell collection filter treatment | $2.0 \times 10^7$/treatment of 20 ml bone marrow fluid | 33 |
|  | After cell collection filter treatment | $1.8 \times 10^7$/treatment of 20 ml bone marrow fluid | Below detection limit |
| Comparative Example 1 | Immediately after trypsin treatment | $0.8 \times 10^6$/treatment of 2 ml bone marrow fluid | 50 |
|  | After washing trypsin | $0.6 \times 10^6$/treatment of 2 ml bone marrow fluid | 3 |

[note 1] ratio when the concentration of a stock trypsin-EDTA solution (TrypLE Select) is regarded as 100%

Next, using the cells cultured in the cell culture container CC, the formation of cartilage was evaluated. The cells cultured and amplified as above were washed with 20 ml of DMEM-high glucose culture medium manufactured by GIBCO BRL once and the cells were collected by centrifugation (1,000 rpm, 10 min, 4° C.).

To a DMEM-high glucose culture medium manufactured by GIBCO BRL, predetermined amounts of additives accelerating cartilage differentiation induction (TGF63 human recombinant, a final concentration of 10 ng/ml; manufactured by Funakoshi; dexamethasone, a final concentration of 100 nM (nmol/l): manufactured by Sigma; ascorbic acid phosphate, a final concentration of 50 μg/ml: manufactured by WAKO; sodium pyruvate, a final concentration of 100 μg/ml: manufactured by COSMO BIO; and L-proline, a final concentration of 40 μg/ml: manufactured by COSMO BIO) were added to prepare a culture medium. To the culture medium, ITS (insulin, transferrin, selenium, bovine serum albumin) was added in an amount of 1/100 of commercially available stock solution to prepare a culture medium. In the culture medium, the mesenchymal cells were suspended so that the concentration was $4 \times 10^5$/ml.

Next, 0.5 ml of the cell suspension was taken and charged into a 15-ml Falcon tube. Then, centrifugation (1,000 rpm, 10 min, 4° C.) of the suspension made the cells into a pellet shape and the tube cap was loosened without treatment. The tube was placed in a 5% $CO_2$ incubator and the cells were cultured at a temperature of 37° C. for 3 weeks.

Figure 4:
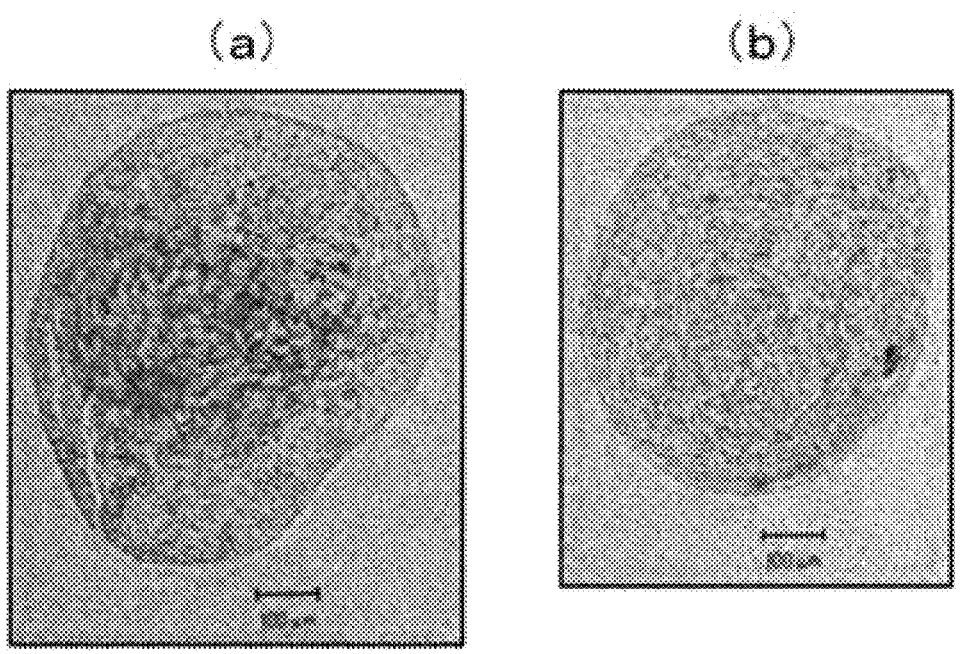
FIGS. 4(a) and 4(b) are pictures showing cartilage formation evaluation results (Alcian blue staining) of collected cells.

During the culture, the culture medium was exchanged twice a week. After the completion of the culture, a spherical cell aggregate was collected, then was fixed with formalin for tissue fixation, and was stained with Alcian blue as a cartilage matrix stain. Observing a tissue section under a microscope, as shown in FIG. 4(a), metachromasis in which a cartilage matrix was stained in blue was observed and it was ascertained that the obtained cells were stem cells with differentiation potential.

Reference Example 1

Cartilage matrix formation ability was evaluated in the same manner as in Example 1 except that the additives accelerating cartilage differentiation induction were not added to a culture medium. As a result, as shown in FIG. 4(b), metachromasis in which a cartilage matrix was stained in purple was not observed.

Comparative Example 1

First, 2 ml of human bone marrow fluid that was the same as that in Example 1 was mixed with 2 ml of phosphate buffer solution (hereinafter, abbreviated as PBS) (two fold dilution).

Next, 3 ml of Ficoll paque plus (GE Healthcare) was charged in a 15-ml centrifuge tube. Then, 4 ml of diluted bone marrow fluid prepared above was layered on the solution. The tube was subjected to centrifugation (1,400 rpm, 30 min, room temperature), thereby collecting a mononuclear cell fraction layer containing adult stem cells.

To the fraction, about 10 ml of PBS was added and the cells were washed by centrifugation (1,300 rpm, 5 min).

Next, in a similar manner, about 10 ml of PBS was added, and the cells were washed again by centrifugation (1,200 rpm, 5 min). The cells after the second washing were suspended in 2 ml of PBS and the number of blood cells was counted, thereby determining the cell collection ratio. The number of cells was also counted in the same manner as in Example 1.

As a result, as shown in Table 1, the collection ratio of red blood cell was less than 1%, the collection ratio of blood platelet was 9%, and the collection ratio of white blood cell was 25%.

The obtained mononuclear cell fraction was suspended in an α-MEM medium (manufactured by GIBCO) and cultured in a 5% $CO_2$ incubator at a temperature of 37° C. for 14 days. During the culture, the culture medium was exchanged every two or three days.

Next, 1 ml of trypsin-EDTA solution (TrypLE Select, manufactured by GIBCO) was added. The cells were allowed to stand in a 5% $CO_2$ incubator at a temperature of 37° C. for 5 minutes and the cells were detached by pipetting. An equal amount of culture medium was further added and the cells were collected by the second pipetting.

As a result, the number of obtained cells was $0.8 \times 10^6$ as shown in Table 2 when 2 ml of bone marrow fluid was treated. The number is converted into about $0.8 \times 10^7$ when 20 ml of bone marrow fluid was treated. The value was 1/2.5 the value obtained by the treatment with the cell separation filter SF.

Then, the suspension was subjected to centrifugation (1,500 rpm, 5 min) to precipitate the cells and a supernatant was removed. Then, physiological saline was added to suspend the cells again. This operation was repeated three times in total, thereby removing the trypsin-EDTA.

As shown in Table 2, the total number of obtained cells was $0.6 \times 10^6$, the collection ratio was 75%, and the concentration of remaining trypsin was 3% where the concentration of the trypsin-EDTA solution (TrypLE Select, manufactured by GIBCO) used for cell detachment was regarded as 100%.

From the experimental results, it was observed that, by using the disposable set for cell culture, the cell culture device, and the cell preparation method of the present invention, mesenchymal stem cells could be obtained in a larger amount than that obtained by density gradient centrifugation method that is currently used as the method for separating adult stem cells and the obtained cells had differentiation potential to cartilage.

The disposable set for cell culture, the cell culture device, and the cell preparation method of the present invention are used to achieve a closed system that has a simple structure without resorting to large scale equipment and that sequentially carries out all of the step of separating useful cells, the step of culturing the useful cells separated in the separation step, and the step of washing and concentrating the cells cultured in the culturing step and can prepare useful cells having high safety and quality, while improving operability.

REFERENCE SIGNS LIST

A Cell separation kit
B Cell collection kit
C1 First cell collection liquid introduction part
C2 Second cell collection liquid introduction part
CC Cell culture container
CF Cell collection filter
D External pressure unit
D1 Air cylinder
D2 Flow path switching valve
E Holder
L0, L1, L11, L12, L2, L21, L3, L31, L32, L4, L5, L51, L6, L7, L8 Pipeline
Lin Liquid inlet
Lout Liquid outlet
P1, P2, P3, P4 Pump
RF Cell filter
SF Cell separation filter
T1 Tank for a liquid to be treated
T2 Cell storage bag
T3 Cell collection tank
T4 Culture medium tank
T5 Cell detaching solution tank
V1, V11, V12, V13, V2, V21, V3, V31, V32, V4, V5, V51, V6, V8 Flow path on-off valve
W1, W2, W3 Drain tank
WA1, WA2 Washing liquid tank

The invention claimed is:

1. A disposable set for cell culture comprising:
(1) a cell culture container having a liquid inlet and a liquid outlet;
(2) a cell separation kit for separating cells used for cell culture, the cell separation kit being connected to the liquid inlet,
wherein the cell separation kit includes a cell separation material selectively trapping cells from a liquid to be treated containing the cells, the cell separation kit includes a cell separation filter storing the cell separation material;
a tank for a liquid to be treated,
wherein the tank stores the liquid to be treated containing cells,
wherein the tank for the liquid to be treated is connected to an upstream side of the cell separation filter via a first pipeline,
a drain tank connected to a downstream side of the cell separation filter via a second pipeline,
a first cell collection liquid introduction part for introducing a cell collection liquid,
wherein the first cell collection liquid introduction part is a syringe storing the cell collection liquid and a plunger of the syringe is pressurized by an external pressure unit driven by gas pressure to supply the cell collection liquid to the cell separation filter,
a piston rod operably connected to the plunger, the plunger having a plurality of positions including a position A and a position B, the piston rod having a plurality of positions including a first position and second position, wherein the piston rod is configured to move from the first position to the second position from the external pressure thereby moving the plunger from position A to position B and thereby pushing out the cell collection liquid and causing the cell collection liquid to flow to the cell separation filter, and wherein the plunger and the piston rod are configured to return to position A and the first position, respectively, through the external pressure unit driven by gas pressure,
the first cell collection liquid introduction part being connected by a pipeline branched at a midway point of the second pipeline, and a third pipeline branched at a midway point of the first pipeline and connected to the liquid inlet of the cell culture container; and a cell storage bag for once storing cells collected by the cell collection liquid introduced from the first cell collection liquid introduction part to the cell separation filter, wherein the cell storage bag is connected to a pipeline branched at a more upstream position of the first pipeline relative to the third pipeline, wherein the once storing cells is a time of collection from the cell separation filter; and (3) a cell collection kit for washing and concentrating cells cultured in the cell culture container, the cell collection kit being connected to the liquid outlet, wherein the cell collection kit includes a cell collection filter storing cell collection material, the cell collection material trapping cultured cells and passing an impurity, a fourth pipeline connected to the liquid outlet of the cell culture container and to an upstream side of the cell collection filter, a drain tank connected to a downstream side of the cell collection filter via a fifth pipeline, a second cell collection liquid introduction part for introducing a cell collection liquid, the second cell collection liquid introduction part being connected by a pipeline branched at a midway point of the fifth pipeline, and a cell collection tank for collecting cells collected by the cell collection liquid introduced from the second cell collection liquid introduction part to the cell collection filter, the cell collection tank being connected by a pipeline branched at a mid a point fourth pipeline.

2. The disposable set for cell culture according to claim 1, wherein the tank for a liquid to be treated is configured as the cell storage bag once storing cells collected by the cell collection liquid introduced from the first cell collection liquid introduction part to the cell separation filter.

3. The disposable set for cell culture according to claim 1, wherein the cell separation filter substantially traps cells useful for cell medicine or regenerative medicine by sending a liquid to be treated containing the cells useful for cell medicine or regenerative medicine and impurity cells to substantially pass the impurity cells through the cell separation filter, and the trapped cells are collected by passing the cell collection liquid in a direction opposite to the direction in which the liquid to be treated is passed.

4. The disposable set for cell culture according to claim 1, wherein a washing liquid tank storing a washing liquid is connected to an upstream side of the cell separation filter via a pipeline.

5. The disposable set for cell culture according to claim 1, wherein at least one of a culture medium tank storing a culture medium and a cell detaching solution tank storing a cell detaching solution containing a cell detaching agent is connected by a pipeline branched at a midway point of the third pipeline.

6. The disposable set for cell culture according to claim 1, wherein the cell collection kit includes a cell collection material trapping cultured cells and passing an impurity.

7. The disposable set for cell culture according to claim 1, wherein a cell filter for removing a cell aggregate is interposed at a midway point of the fourth pipeline.

8. The disposable set for cell culture according to claim 1, wherein the cell collection filter traps cultured cells by passing a cell suspension containing the cells cultured in the cell culture container and the trapped cells are collected by passing the cell collection liquid in a direction opposed to the direction in which the cell suspension is passed.

9. The disposable set for cell culture according to claim 1, wherein the second cell collection liquid introduction part is a syringe storing the cell collection liquid and a plunger of the syringe is pressurized by an external pressure unit driven by gas pressure to supply the cell collection liquid to the cell collection filter.

10. The disposable set for cell culture according to claim 1, wherein a washing liquid tank storing a washing liquid is connected to an upstream side of the cell collection filter via a pipeline.

11. A cell culture device using the disposable set for cell culture according to claim 1, the cell culture device comprising:
a flow path on-off valve for opening and closing a flow path by pinching the pipeline and a pump sequentially pressurizing the pipeline, the flow path on-off valve and the pump being provided at an appropriate position of the pipeline of the disposable set for cell culture; and
a controller controlling opening and closing of the flow path on-off valve and controlling driving of the pump.

12. A cell culture device using the disposable set for cell culture according to claim 1, the cell culture device comprising:
a flow path on-off valve for opening and closing a flow path by pinching the pipeline and a pump sequentially pressurizing the pipeline, the flow path on-off valve and the pump being provided at an appropriate position of the pipeline of the disposable set for cell culture; and
a controller controlling opening and closing of the flow path on-off valve, controlling driving of the pump, and controlling driving of the external pressure unit.

13. The cell culture device according to claim 12, wherein the compressed gas is supplied from a gas cylinder storing the compressed gas.

14. The cell culture device according to claim 13, wherein the compressed gas is carbon dioxide.

15. A cell preparation method using the cell culture device according to claim 11, the method sequentially carrying out a step of separating useful cells to be seeded, a step of culturing the useful cells separated in the separation step, and a step of washing and concentrating the cells cultured in the culturing step, in a closed system.

16. A cell culture device using the disposable set for cell culture according to claim 9, the cell culture device comprising:
a flow path on-off valve for opening and closing a flow path by pinching the pipeline and a pump sequentially pressurizing the pipeline, the flow path on-off valve and the pump being provided at an appropriate position of the pipeline of the disposable set for cell culture;
wherein the second cell collector liquid introduction part is configured than an external pressure unit pressurizing the plunger of the syringe, the external pressure unit being driven by compressed gas; and
a controller controlling opening and closing of the flow path on-off valve, controlling driving of the pump, and controlling driving of the external pressure unit.

17. The disposable set for cell culture according to claim 1, wherein the plunger of the syringe is pressurized by an external pressure is 0.05 MPa to 1 MPa.

18. A disposable set for cell culture comprising:
(1) a cell culture container having a liquid inlet and a liquid outlet;
(2) a cell separation kit for separating cells used for cell culture, the cell separation kit being connected to the liquid inlet,
wherein the cell separation kit includes a cell separation material selectively trapping cells from a liquid to be treated containing the cells, the cell separation kit includes a cell separation filter storing the cell separation material, wherein the cell separation material is composed of fiber or fiber aggregate, the fiber or fiber aggregate has a diameter from 3 to 40 μm, the cell separation material has a density in a range from $1.0\times10^4$ to $1.0\times10^6$ g/m$^3$, wherein the density is a value obtained by dividing the weight (g) of a cell separation material by the volume (m$^3$), the cell separation material has an opening size of 3 μm or more in minor axis and an opening size of 120 μm or less in major axis, wherein the opening size is a mean value determined as follows:

observing the cell separation material under a scanning electron microscope to give a micrograph;

determining a major diameter and a minor diameter of a substantial hole formed by the intersections of two or more different fibers at fifty or more points with an image analyzer; and calculating each mean value calculated from the determined diameters;

a tank for a liquid to be treated;

wherein the tank stores the liquid to be treated containing cells, wherein the tank for the liquid to be treated is connected to an upstream side of the cell separation filter via a first pipeline, a drain tank connected to a downstream side of the cell separation filter via a second pipeline, a first cell collection liquid introduction part for introducing a cell collection liquid, wherein the first cell collection liquid introduction part is a syringe storing the cell collection liquid and a plunger of the syringe is pressurized by an external pressure unit driven by gas pressure to supply the cell collection liquid to the cell separation filter, a piston rod operably connected to the plunger, the plunger having a plurality of positions including a position A and a position B, the piston rod having a plurality of positions including a first position and second position, wherein the piston rod is configured to move from the first position to the second position from the external pressure thereby moving the plunger from position A to position B and thereby pushing out the cell collection liquid and causing the cell collection liquid to flow to the cell separation filter, and wherein the plunger and the piston rod are configured to return to position A and the first position, respectively, through the external pressure unit driven by gas pressure, the first cell collection liquid introduction part being connected by a pipeline branched at a midway point of the second pipeline, and a third pipeline branched at a midway point of the first pipeline and connected to the liquid inlet of the cell culture container;

a cell storage bag for once storing cells collected by the cell collection liquid introduced from the first cell collection liquid introduction part to the cell separation filter, wherein the cell storage bag is connected to a pipeline branched at a more upstream position of the first pipeline relative to the third pipeline, wherein the once storing cells is a time of collection from the cell separation filter; and (3) a cell collection kit for washing and concentrating cells cultured in the cell culture container, the cell collection kit being connected to the liquid outlet, wherein the tank for a liquid to be treated is configured as the cell storage bag once storing cells collected by the cell collection liquid introduced from the first cell collection liquid introduction part to the cell separation filter, wherein the cell separation filter substantially traps cells useful for cell medicine or regenerative medicine by sending a liquid to be treated containing the cells useful for cell medicine or regenerative medicine and impurity cells to substantially pass the impurity cells through the cell separation filter, and the trapped cells are collected by passing the cell collection liquid in a direction opposite to the direction in which the liquid to be treated is passed, and wherein a washing liquid tank storing a washing liquid is connected to an upstream side of the cell separation filter via a pipeline.

* * * * *